United States Patent [19]

Fukukita et al.

[11] Patent Number: 4,936,308

[45] Date of Patent: Jun. 26, 1990

[54] METHOD AND APPARATUS FOR MEASURING ACOUSTIC CHARACTERISTICS AND TEMPERATURE

[75] Inventors: Hiroshi Fukukita, Tokyo; Shinichiro Ueno, Machida, both of Japan

[73] Assignees: Agency of Industrial Science & Technology; Ministry of International Trade & Industry, both of Tokyo, Japan

[21] Appl. No.: 265,519

[22] Filed: Nov. 1, 1988

[30] Foreign Application Priority Data

May 27, 1988 [JP] Japan .................................. 63-128214

[51] Int. Cl.$^5$ ............................................. A61B 8/00
[52] U.S. Cl. ............................... 128/660.02; 128/736
[58] Field of Search ..................... 128/660.01, 660.02, 128/660.03, 660.06–660.07, 736; 73/547, 549, 602; 374/117

[56] References Cited

U.S. PATENT DOCUMENTS

| | | | |
|---|---|---|---|
| 4,566,460 | 1/1986 | Sato et al. ........................ | 128/660.02 |
| 4,610,255 | 9/1986 | Shimura et al. ................. | 128/660.07 |
| 4,754,760 | 7/1988 | Fukukita et al. ................ | 128/660.02 |
| 4,817,615 | 4/1989 | Fukukita et al. ................ | 128/660.02 |

FOREIGN PATENT DOCUMENTS 60-119926  6/1985  Japan ............................... 128/660.07

*Primary Examiner*—Francis Jaworski
*Attorney, Agent, or Firm*—Oblon, Spivak, McClelland, Maier & Neustadt

[57] ABSTRACT

An acoustic characteristic measurement method comprising transmitting into a specimen an ultrasonic probe pulse and a pulse formed by the superposition of the probe pulse centroid on a pump pulse of a lower frequency than that of the probe pulse at a portion where the particle acceleration of the pump pulse is at a peak, receiving reflections of the transmitted signal from two or more reflecting points that are at different depths in the specimen, frequency-analyzing the received signals and obtaining a spectral ratio, and using the spectral ratio to measure the distribution in the specimen of the degree of spectral separation and the crossover frequency.

14 Claims, 8 Drawing Sheets

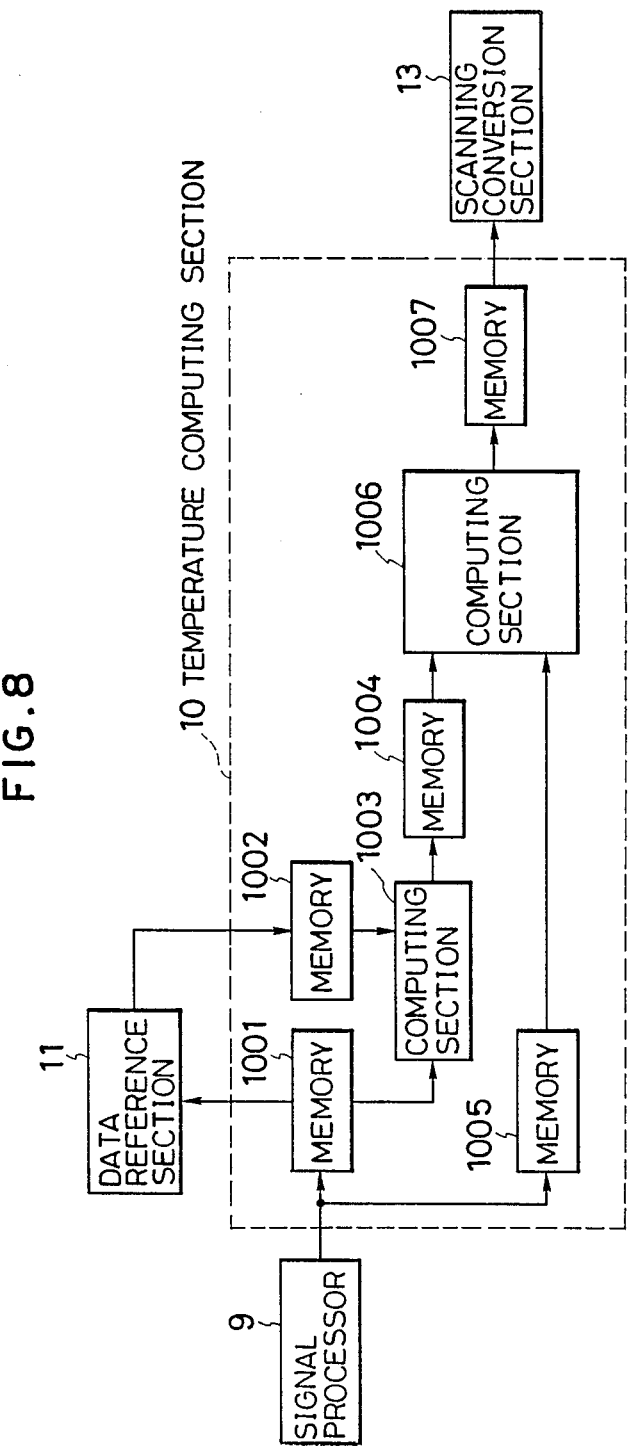

METHOD AND APPARATUS FOR MEASURING ACOUSTIC CHARACTERISTICS AND TEMPERATURE

BACKGROUND OF THE INVENTION

1. Field of the Invention

The present invention relates to a method and apparatus in which ultrasonic waves are used to determine temperature changes inside tissue in vivo by utilizing the temperature dependency of the acoustic characteristics of the tissues as obtained by, for example, transmitting ultrasonic waves into the tissue and receiving the reflections of these waves.

2. Prior Art Statement

Ultrasonic diagnostic devices are known which perform measurements in vivo by means of ultrasonic waves. Most of these ultrasonic diagnostic devices employ the pulse reflection method in which the measurements are performed by transmitting ultrasonic pulses into the living tissue and using information obtained from the pulses reflected back from the tissue. In the pulse reflection method, internal information on the tissue comprised of the strength, i.e., the amplitude, of the reflections from boundaries in the tissue where there are changes in acoustic impedances and the propagation delay times is gathered two-dimensionally to provide a tomographic image. However, in recent years there has been increasing demand for ultrasonic diagnostic apparatuses which can be used to obtain other information in addition to that relating to the shape of in vivo tissues. One example of such information is the internal temperature of the tissue. The ability to obtain internal temperature information in vivo would make it possible to monitor the temperature during cancer thermotherapy. Temperature can be deduced in vivo by measuring acoustic characteristics such as, for example, ultrasonic wave attenuation, sonic velocity, the non-linearity parameter B/A and the like, followed by comparison of the measured values with those obtained through prior investigation of the temperature dependency characteristics of such acoustic characteristics. A method that is known relating to obtaining information relating to the non-linearity parameter was disclosed in Japanese Laid-open patent publication No. 60(1985)-119926, and will be described briefly here.

This method uses the non-linearity of the dependence of the sonic propagation velocity on the wave particle velocity or sound pressure. Because of this, transmitted into the tissue are a relatively high-frequency probe pulse from a transmit/receive oscillator, and a relatively low-frequency pump pulse from a location substantially the same as that of the probe pulse and in the same direction. The drive timing of the probe pulse oscillator and the pump pulse oscillator is adjusted so that the measurement probe wave is superposed on the pump wave at the positive particle velocity portion, as shown in FIG. 9 (a) (or at the negative particle velocity portion, as in FIG. 9 (b)). By then obtaining the difference in phase between the reflected probe pulse signal received when both pump pulse and probe pulse are transmitted into the tissue, and the phase of the reflected probe pulse signal received when only the measurement pulse is transmitted, or of the signal received when the transmission is of both pump pulse and probe pulse, arranged so that the phase is reversed compared with the initial transmission, the phase modulation of the measurement pulse arising from the effect of the pump wave alone is detected using the reflected pulse method, to thereby obtain the acoustic non-linearity parameter B/A of the tissue. Thus, when attention is focused on the progress of the probe pulse, the probe pulse is phase modulated by an amount decided by the traversed-distance integral of the product of the non-linearity parameter of the region traversed by the probe pulse until reaching a reflector (a position function), and the pulse wave amplitude. Utilizing this, the signals being reflected back from different depths are received and demodulated and the changes in the phase signals thus obtained are found, and depthwise differentiation is also used to obtain the distribution of the non-linearity parameter B/A.

In the said conventional non-linearity parameter measurement method, however, because the probe pulse superposition is at the particle velocity positive (or negative) peak portions of the pump pulse, at instants in which the particle velocities of both pulses which are on the increase are compounded, the velocity becomes very high, which produces abnormal distortion in the probe pulse and adversely affects the measurement, and there is also a risk to the safety of the living body. In addition, the only acoustic characteristics obtained are those relating to the non-linearity parameter, with no provision to simultaneously obtain other information, for example attenuation characteristics, and as such it is impossible to measure temperature with high reliability.

The present inventors have also proposed (Ref. U.S. Pat. No. 4,754,760) a method of obtaining the internal temperature. This method consists of transmitting pump pulses and probe pulses into a specimen, obtaining the variations in delay times from non-linearity interactions and the crossover frequencies of the spectral distributions of the received signals corresponding to the respective phase states of the pump pulses and probe pulses produced in the specimen. By also varying the strengths of a multiplicity of pump pulses to change the delay time variations and finding the crossover frequencies, the center frequency of the spectral distributions of the received signals can be found with good precision. The ultrasonic wave attenuation characteristics can then be obtained from changes in these center frequencies at different depths, and the amount of temperature change found from variations in the ultrasonic wave attenuation characteristics.

OBJECT AND SUMMARY OF THE INVENTION

The object of the present invention is to provide a method and apparatus for measuring acoustic characteristics and temperature whereby acoustic characteristics can be measured without subjecting the probe pulses to abnormal distortion or risking the safety of the living body, and temperatures can be measured with improved reliability.

In order to achieve the aforesaid object, the acoustic characteristic measurement method according to this invention comprises transmitting into the specimen an ultrasonic probe pulse and a pulse formed by the superposition of the probe pulse centroid on a pump pulse of a lower frequency than that of the probe pulse at a portion where the particle acceleration of the pump pulse is at a peak, receiving reflections of the transmitted signal from two or more reflecting points that are at different depths in the specimen, frequency-analyzing the received signals and obtaining the spectral ratio, and from the spectral ratio measuring the distribution in the specimen of the degree of spectral separation and the crossover frequency.

It also comprises obtaining the spectral shift in the received signals, and using the amount of phase shift and the degree of spectral separation to measure the frequency dependency characteristic of the sonic attenuation characteristics in the specimen.

It also comprises obtaining the associated non-linearity coefficient from the degree of spectral separation and the sonic attenuation coefficient from the crossover frequency and degree of spectral separation, and also obtaining the associated non-linearity coefficient from the degree of spectral separation and measuring the sonic attenuation coefficient from the crossover frequency.

Also, in order to achieve the aforesaid object the temperature measurement method according to this invention comprises measuring the change in temperature in the specimen before and after the heating thereof on the basis of the aforementioned temperature dependency characteristic of the acoustic characteristics.

The said method also comprises measuring the change in temperature in the specimen before and after the heating thereof on the basis of the temperature dependency characteristic of the attenuation coefficient with reference to the associated non-linearity coefficient in the region of interest.

In order to achieve the aforesaid object, the acoustic characteristic measurement apparatus according to this invention comprises an ultrasonic wave transducer for transmitting an ultrasonic probe pulse and a pump pulse of a lower frequency than that of the probe pulse; means for controlling the phasal relationship between the probe pulse and the pump pulse; means for frequency analysis of the signals received by the ultrasonic wave transducer; and signal processing means for computing the spectral ratio, crossover frequency and degree of spectral separation on the basis of the output of the frequency analysis means.

The signal processing means also computes at least one of the associated non-linearity coefficient and sonic attenuation coefficient from the crossover frequency and the degree of spectral separation.

In order to achieve the aforesaid object, in addition to the acoustic characteristic measurement apparatus the temperature measurement apparatus according to this invention is also provided with a temperature computing section which measures temperature changes based on measurement of acoustic characteristics before and after heating of the specimen.

Preferably the temperature computing section compares the acoustic characteristic values with data in a data reference section and temperature changes are measured on the basis of temperature dependency characteristics thus obtained.

In accordance with the configuration of the invention as described in the foregoing, by superposing the probe pulse centroid on the pump pulse at an intermediate portion between the negative and positive particle velocity peaks, i.e., the particle acceleration peak portion, the particle velocity peak produced by compounding the two pulses can be made around the same as the particle velocity of the pump pulse itself; also, the oscillator drive timing is adjusted so that the probe wave pulse superposition is at the positive particle acceleration peak portion of the pump wave; and the ratio of the spectrum of the reflected signals received when both pump pulse and probe pulse are transmitted, to the spectrum of the received signals obtained when the pump and probe pulses are transmitted so that the pump pulse phase is reversed, i.e., so that the probe pulse is superposed when the pump wave particle acceleration is at a negative peak, that is, the spectral ratio, is measured as well as the crossover frequency obtained from the spectral ratio and the slope of the spectral ratio. Also, the attenuation factor and the non-linearity parameter in the specimen, and changes in temperature from these acoustic characteristics, are utilized to obtain temperature changes in the specimen.

Other objects and features of the invention will become clear from the following explanation made with reference to the accompanying drawings.

BRIEF DESCRIPTION OF THE DRAWINGS

FIG. 8 is a block diagram showing details of the functional parts of an example of the temperature computing section used in the ultrasonic temperature measurement apparatus.

DETAILED DESCRIPTION OF THE PREFERRED EMBODIMENTS

Figure 1A:
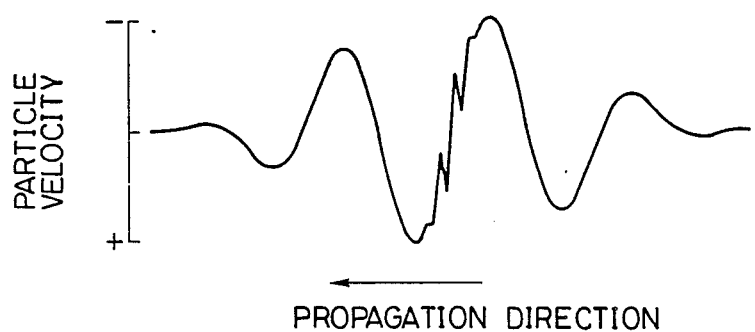
FIGS. 1 (a) and (b) show the superposed state of the pump pulse and probe pulse to explain the principle of the acoustic characteristic measurement method according to an embodiment of the present invention.

First, the principle of the method of measurement employed by the present invention will be described with reference to FIG. 1.

The velocity of an ultrasonic wave of infinitely small amplitude in a propagating medium is assumed to be $C_0$, the density $P_0$, and the acoustic non-linearity parameter $B/A$. In the case of the propagation velocity of a sound wave of a finite amplitude where particle velocity at any point in the waveform is u and the sound pressure is p, the sonic velocity C at any point can be found from the following equations (1), (2), and (3).

$$C = C_0 + u + \frac{B}{2A} \cdot \frac{p}{P_0 C_0} \quad (1)$$

$$= C_0 + (1 + B/2A)u \quad (2)$$

$$= C_0 + \beta u \quad (3)$$

Usually, $(1+B/2A)$ is referred to as the coefficient of non-linearity $\beta$.

As is apparent from these relationship equations, the sonic velocity increases at portions where the pump wave particle velocity is positive, and decreases at portions where the pump wave particle velocity is negative. Therefore, in intermediate portions when particle velocity is changing over from negative to positive, i.e., at portions where particle acceleration is positive, the pump waveform is compressed as the wave propagates and, conversely, at portions where particle acceleration is negative, the propagation of the wave is accompanied by stretching of the pump waveform. Thus, when the probe waveform is superposed on a portion of the pump wave where the particle acceleration is positive, as shown in FIG. 1 (a), the propagation is accompanied by a compression of the probe waveform, increasing the amplitude; that is, the wave spectrum expands toward the high-frequency side. Conversely, when the probe waveform is superposed on a portion of the pump wave where the particle acceleration is negative, as shown in FIG. (b), the probe pulse is stretched, decreasing the amplitude and contracting the spectrum toward the low-frequency side. In a medium where there is no attenuation, the spectrum modulation characteristic based on the above type of probe pulse propagation can be approximated analytically, as follows.

$$H\pm(\omega)=H\{\omega(1\mp\Omega\tau)\} \quad (4)$$

Here, $\omega$ is angular frequency; $H(\omega)$ is the spectrum of the probe pulse before modulation; $H\pm(\omega)$ is the spectrum of the probe pulse after modulation; the symbol $\pm$ stands for the particle acceleration at the superposed portion of the pump wave; $\Omega$ is the center angular frequency of the pump wave; $\tau$ is the difference between the propagation delay time at the peak portion of the pump wave particle velocity and the propagation delay time at the zero particle velocity portion, with respect to a distance d.

$$\begin{aligned}\tau &= d(1/C_0 - 1/C) & (5)\\ &\approx d\cdot\beta V_0/C_0^2 & (6)\\ &= t_0\cdot\beta V_0/C_0 & (7)\\ &= t_0\cdot\beta P_0/(P_0 C_0^2) & (8)\end{aligned}$$

Here, $V_0$ is the amplitude of the pump wave particle velocity; $P_0$ is the pump wave sonic amplitude; and $t_0$ is propagation delay time ($=d/C_0$).

The said probe pulse modulation characteristic can be obtained analytically on condition that the length l of the probe pulse is sufficiently smaller than the wavelength $\Lambda$ of the pump wave.

However, in practice this condition can be relaxed. Even with the conditions shown by the following equation, numerical simulation shows that equation (4) is approximately valid.

$$l<\Lambda/2 \quad (9)$$

If the probe pulse is assumed to be an RF pulse with a Gaussian envelope, the pulse spectrum $H(\omega)$ can be approximated by the equation:

$$H(\omega)=(\text{constant})\cdot\exp\{-(\omega-\omega_c)^2/2\sigma_0^2\} \quad (10)$$

Here, $\omega_c$ is center angular frequency and $\sigma_0^2$ is spectral dispersion.

In this case, the modulated spectra $H+(\omega)$ and $H-(\omega)$ coincide, and the crossover frequency $\omega_x$ is equal to $\omega_c$.

$$H+(\omega_c)=H-(\omega_c) \quad (11)$$

The relationship shown in equation (11) is obtained when spectrum $H(\omega)$ waveform is symmetrical with respect to center angular frequency $\omega_c$. Whatever the case, the crossover frequency $\omega_x$ of the spectra $H+(\omega)$ and $H-(\omega)$ of the equation (10) spectrum $H(\omega)$ modulated in a medium where there is no attenuation is equal to $\omega_c$.

The function of the ratio of the modulated spectra estimated logarithmically will be referred to as the spectral ratio $R(\omega)$.

$$R(\omega)=\ln\{H-(\omega)/H+(\omega)\} \quad (12)$$

Also, the slope at the crossover frequency $\omega_x$ of the spectral ratio $R(\omega)$ will be referred to as the degree of spectral separation DSS.

$$DSS=\delta\{R(\omega)\}/\delta\omega|\omega-\omega_x \quad (13)$$

With respect to the probe pulse spectrum shown in equation (10), the spectral ratio $R(\omega)$ and the degree of spectral separation DSS become:

$$R(\omega)=-2\Omega\tau(\omega-\omega_c)\omega/\sigma_0^2 \quad (14)$$

$$DSS=-2\Omega\tau\omega_c/\sigma_0^2 \quad (15)$$

In equation (15), as $\Omega$, $\omega_c$ and $\sigma_0^2$ are known quantities, the propagation delay time difference $\tau$ can be found by measuring DSS. If $\tau$ is obtained, by providing the pump wave particle velocity amplitude $V_0$ or sound pressure amplitude $P_0$ in equations (6) to (8) the various acoustic characteristics $\beta/C_0^2$, $\beta/C_0$, and $\beta/P_0 C\sigma_0^2$ can be estimated. The acoustic characteristics relating to these non-linearity coefficients $\beta$ will be collectively referred to as the associated coefficient of non-linearity $\beta'$.

In the foregoing, the principle of obtaining the associated coefficient of non-linearity $\beta'$ from the spectral modulation characteristics of the probe pulse in a medium having no attenuation has been described. This principle can be extended to apply to a propagation medium having the same type of frequency-dependent attenuation characteristics as living tissue. In this case, the result is that the crossover frequency $\omega_x$ depends on the attenuation coefficient of the propagating medium, and the attenuation coefficient can be estimated from changes in $\omega_x$, and with respect to the associated coefficient of non-linearity $\beta'$, virtually the same type of treatment as in the case of no attenuation is possible. The spectral modulation characteristic $H\pm(\omega)$ of the probe pulse in an attenuating medium is obtained analytically, as shown below, and the relationship of the modulation characteristics and the acoustic characteristics of the medium is clarified and an algorithm derived for finding the attenuation characteristics and the associated coefficient of non-linearity $\beta'$ from the received signals of the modulated ultrasonic wave. Generally, regarding non-linear distortion produced by propagation in an attenuating medium, by dividing the overall propagation delay time into very short time periods $\Delta t$ and regarding it as two separate phenomena arising in the intervals between time periods, that is, (i) linear attenuation, and (ii) non-linear distortion when there is no attenuation, it is possible to describe it as an accumulation over the overall propagation delay time. Attenuation characteristic $\alpha_j(\omega)$ in the $j(1 \leq j \leq i)$th time period $\Delta t$ can be shown by the following.

$$\alpha_j(\omega) = A_j \cdot (\omega/\omega_0)^n \cdot \Delta t \qquad (16)$$
$$= a_j \omega^n$$

Here, $A_j$ is the attenuation per unit time at a reference frequency $\omega_0$ (neper/unit time). n represents the parameter of attenuation frequency dependency, for soft tissue in vivo a value of 1-2 is assumed; here, n is taken to be a constant. $a_j$ is the attenuation coefficient.

A very short distance $\Delta x_j$ corresponding to the very short time periods j can be shown by the following equation, using the sonic velocity $C_{0j}$ of an infinitely small amplitude in the intervals between time periods.

$$\Delta X_j = C_{0j} \cdot \Delta t \qquad (17)$$

Also, if the propagation delay time differences accumulated up to time period j is $\tau_j$, the difference $\Delta \tau_j$ between $\tau_j$ and $\tau_{j+1}$ can be shown by the following equations.

$$\Delta \tau_j = \tau_{j+1} - \tau_j \qquad (18)$$
$$= \Delta x_j(1/C_{0j} - 1/C_j) \qquad (19)$$
$$\approx \Delta x_j \beta_j U_{0j}/C_{0j}^2 \qquad (20)$$
$$= \Delta t \beta_j U_{0j}/C_{0j} \qquad (21)$$
$$= \Delta t \beta_j P_{0j}/(P_{0j} C_{0j}^2) \qquad (22)$$

Equations (19) to (22) correspond to equations (5) to (8).

Thus, if an attenuation coefficient $a_j$ and a propagation delay time difference $\tau_j$ are designated, probe pulse modulation characteristic $H\pm(\omega)$ accumulated up to time period j can be analytically found as follows. With respect to the spectrum of the probe wave prior to receiving distortion, shown in equation (10), the results of modulation produced in time periods $j=1$ by the action of (i) linear attenuation and (ii) non-linear distortion when there is no attenuation will be as follows.

$$(i) \ldots H(\omega) \cdot \exp(-a_1 \cdot \omega^n) \qquad (23)$$

$$(ii) \ldots H\{\omega(1\pm\Omega\tau_1)\} \cdot \exp[-a_1 \cdot \{\omega(1\mp\Omega\tau_1)\}^n] \qquad (24)$$

The effect of non-linear distortion in time periods $j=2$ with respect to the angular frequency $\omega$ will then be $\omega \cdot (1\mp\Omega\tau_2)/(1\mp\Omega\tau_1)$. The results of the modulations will be:

$$(i) H\{\omega(1\mp\Omega\tau_1)\} \cdot \exp[-a_1 \cdot \{\omega(1\mp\Omega\tau_1)\}^n] \times \exp(-a_2 \cdot \omega^n) \qquad (25)$$

$$(ii) H\{\omega(1\mp\Omega\tau_2)\} \cdot \exp[-a_1 \cdot \{\omega(1\mp\Omega\tau_2)^n\}] \times \exp\left[-a_2 \cdot \left(\omega \frac{1\mp\Omega\tau_2}{1\mp\Omega\tau_1}\right)^n\right] \qquad (26)$$

From the above, the spectrum $\pm(\omega)$ modulated by the action of the linear attenuation and non-linear distortion accumulated in all of the time periods j can be shown by the following equations.

$$H\pm(\omega) = H\{\omega(1\mp\Omega\tau_i)\} \times \qquad (27)$$
$$\exp\left(-\omega^n(1\mp\Omega\tau_i)^n \sum_{j=1}^{i} \frac{a_j}{1\mp\Omega\tau_{j-1}}\right)$$

$$= \exp[-\{\omega(1\mp\Omega\tau_i) - \omega_c\}^2/2\sigma_0^2 - \omega^n a\pm] \qquad (28)$$

-continued $$a\pm = (1\mp\Omega\tau_i)^n \sum_{j=1}^{i} \frac{a_j}{1\mp\Omega\tau_{j-1}} \qquad (29)$$

Thus, from equation (28), spectral ratio $R(\omega)$ is $$R(\omega) = \ln[H-(\omega)/H+(\omega)] \qquad (30)$$
$$= -2\omega\Omega\tau_i(\omega - \omega_c)/2\sigma_0^2 - \omega^n(a_- - a_+)i$$

At a crossover frequency $\omega_{xj}$, $R(\omega)=0$, therefore from equation (30)

$$\omega_{xj} - \omega_c = \sigma_0^2 \cdot \omega_{xj}^{n-1}(a_- - a_+)/2\Omega\tau_i \qquad (31)$$

In equation (31), as $\omega_c$ and $\sigma_0^2 \Omega$ are known quantities and $\omega_{xj}$ is a measurable quantity that can be obtained from the received signals, as shown below, information $(a_- - a_+)i$ relating to the attenuation coefficient can be obtained by measuring the value of $\tau_j$ and assuming an n value. Here, $\tau_j$ and the value of n can be obtained, as in the following equation, from the slope of the spectral ratio crossover frequency $\omega_{xj}$, i.e., from the degree of spectral separation DSS.

$$DSS = \delta\{R(\omega)\}/\delta\omega \qquad (32)$$
$$= 2\Omega\tau_i\{\omega_{xj} - (n-1)(\omega_{xj} - \omega_c)\}/\sigma_0^2$$

In equation (32), DSS is a measurable quantity that can be obtained from the received signals as described below, so that by assuming a value for n, with respect to $\tau_j$ measurement is possible by a known prior method, and as such, the value of n can also be determined from equation (29).

The method of measuring the various acoustic characteristics the relationships of which have been clarified in the above, such as $\omega_{xj}$ and $\tau_j (a_- - a_+)$, also attenuation coefficient $a_j$ and the distribution of associated coefficient of non-linearity $\beta_j'$ in the direction of propagation, the method of using the measured acoustic characteristics to determine temperature changes in the propagating medium, and the apparatus for these measurements, will now be described with reference to the accompanying drawings.

Figure 2:
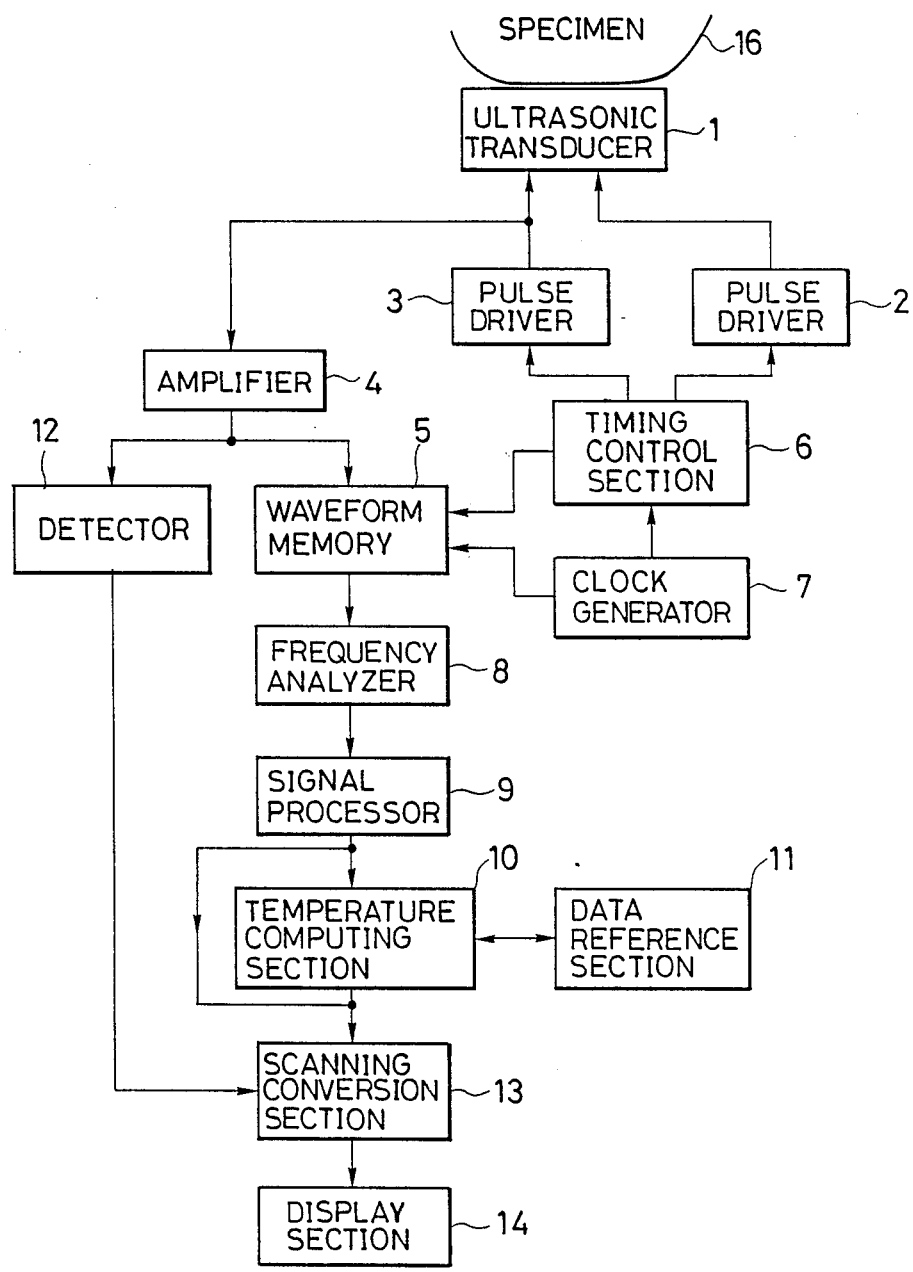
FIG. 2 is a block diagram showing the functional parts of an embodiment of an ultrasonic temperature measurement apparatus according to this invention.

FIG. 2 shows a functional block diagram of an embodiment of an ultrasonic temperature measurement apparatus according to the present invention. The basic principle of the present invention is that of the ultrasonic pulse reflection method in which echoed signals are received. In FIG. 2, 1 is an ultrasonic transducer that transmits and receives pump pulses and probe pulses; 2 is a pulse driver that applies pump wave drive pulses to the ultrasonic transducer 1;3 is a pulse driver that applies probe wave drive pulses to the ultrasonic transducer 1; 4 is an amplifier for amplifying the received signals output by the ultrasonic transducer 1; 5 is a waveform memory for storing the output of the amplifier 4; 6 is a timing control section for controlling the timing of the pulse drivers 2 and 3 and the waveform memory 5. The numeral 7 denotes a clock generator that supplies clocks to the waveform memory 5 and the timing control section 6; 8 is a frequency analyzer that performs Fourier transformations on the waveform stored in the waveform memory 5; 9 is a signal processor that processes the signals output by the frequency analyzer 8 and obtains the acoustic characteristics; 10 is a temperature computing section that computes the temperature from the output of the signal processor 9; 11 is a data reference section that outputs information on the temperature dependency of the acoustic characteristics for the temperature computing section 10; 12 is a detector that detects the output of the amplifier 4; 13 is a scanning conversion section that produces images of the distribution of the acoustic characteristics from the output of the signal processor 9, images of the temperature distribution from the output of the temperature computing section 10 and B-mode tomographic images from the output of the detector 12. Numeral 14 denotes a display section that displays the output of the scanning conversion section 13, and 16 is a specimen (a living body).

Figure 3:
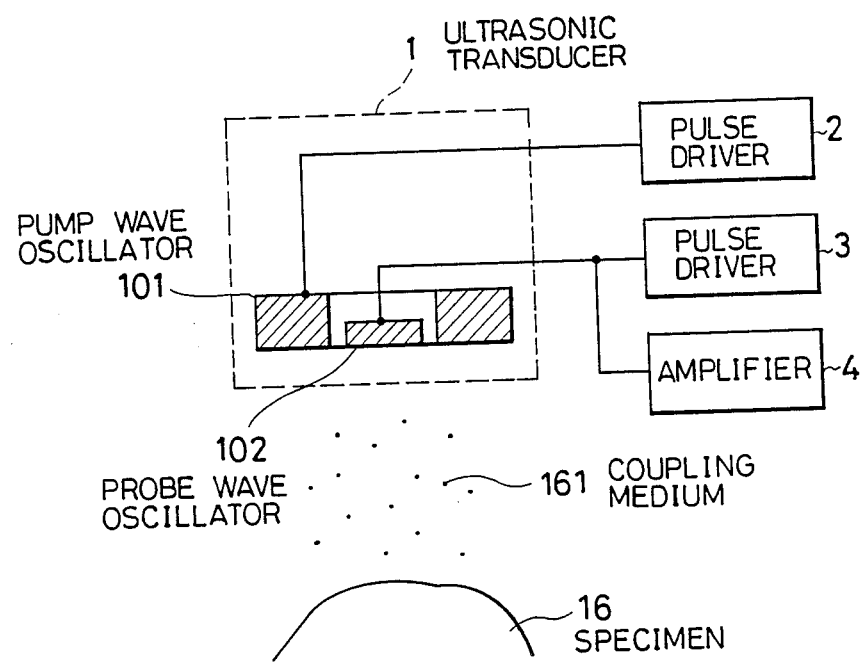
FIG. 3 shows an example configuration of an ultrasonic transducer employed in the ultrasonic temperature measurement apparatus.

FIG. 3 shows an example of a preferred configuration for the ultrasonic transducer 1 employed in the ultrasonic temperature measurement apparatus. As shown in FIG. 3, the ultrasonic transducer 1 is constituted of a pump wave oscillator 101 and a probe wave oscillator 102. The pump wave oscillator 101 is, for example, a ring-shaped piezo-electric oscillator with a center frequency of 300 KHz, an outside diameter of 60 mm and an inside diameter of 20 mm, while the probe wave oscillator 102 is a focussing type piezo-electric oscillator with a center frequency of 3 MHz and a outside diameter of 20 mm. The output level of the pump wave oscillator 101 is a particle velocity amplitude of 250 mm/s and a peak output in water of 4 W/cm$^2$, while the output level of the probe wave oscillator 102 is in the order of what is generally used for an ultrasonic diagnostic apparatus, or slightly lower than that. Preferably the spectral characteristic of the probe pulse is gaussian, and the frequency characteristics of the probe wave oscillator 102 and the frequency characteristics of the drive pulses of the pulse driver 3 are adjusted for that purpose. To prevent high-frequency components of the pump pulse frequency characteristics from being included in the frequency band of the probe pulse characteristics, high-frequency components in the output are suppressed at the pulse driver 2.

Figure 9A:
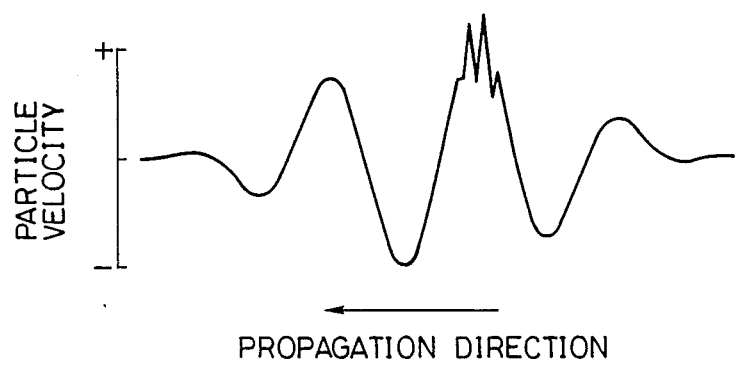
FIGS. 9 (a) and (b) show superposed states of the pump pulse and probe pulse using a conventional acoustic characteristic measurement method.
Figure 9B:
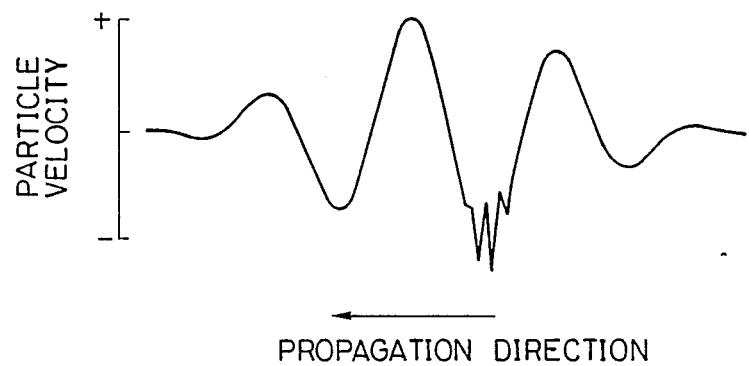

The pump pulse transmitted by the pump wave oscillator 101 and the probe pulse transmitted by the probe wave oscillator 102 cross and are superposed in a coupling medium 161, and then impinge on the specimen 16. A fluid such as water is a suitable choice for the coupling medium 16, for which the selected depth, that is, the distance between the ultrasonic emission surface of the probe wave oscillator 102 and the specimen 16, is for example around 100 mm. The probe pulse is modulated in the course of the propagation of the superposed pulses in the specimen 16. The modulation characteristics depend on which part of the pump pulse the centroid of the probe pulse is superposed. The superposition state is used as a basis for the following classification: phasal relationship A, when the superposition is at the positive peak of the pump wave particle velocity, as in FIG. 9 (a); phasal relationship B, when it is at the negative peak of particle velocity, as in FIG. 9 (b); phasal relationship C, when it is at the positive peak of particle acceleration, as in FIG. 1 (a); and phasal relationship D, when it is at the negative peak of particle acceleration, as in FIG. 1 (b).

The mutual timing of the drive pulse generation by the pulse drivers 2 and 3 to control these phasal relationships is controlled by timing control section 6. In practice, the time relationship of the operation of probe wave pulse driver 3 and waveform memory 5 is fixed, and the pulse generation timing of the pump wave pulse driver 2 is controlled, or the polarity of the drive pulses is reversed. Time-based resolution of the timing control is in the order of 1/64th of a single pump wavelength, which in this case will be about 50 ns. Such time control can be realized by digital delay techniques, using a 50 ns (20 MHz) clock signal, preset counters, and the like. This clock signal is supplied from the clock generator 7.

The probe pulse in which the phasal relationship of the superposition is thus controlled is modulated in accordance with each phase state as it propagates in the specimen 16 and is reflected back by the acoustic scattering characteristics of the specimen 16, and arrives at the probe wave oscillator 102 where it is converted to a received signal. Although not shown, the entire ultrasonic transducer 1 may be swung by a mechanical scanning mechanism for sector scanning, for example. The received signal is amplified by the amplifier 4 and is stored in the waveform memory 5. The waveform memory 5 is constituted of, for example, an A/D converter and high-speed memory. Preferably the frequency of the A/D converter sampling clock is at least four times the frequency of the received signal, which is 3 MHz; here, a frequency of 20 MHz is appropriate. The sampling clock is supplied from the clock generator 7. A data window is used to sample the required position and length portions of the received signals stored in the waveform memory 5, and this data is Fourier-transformed by the frequency analyzer 8. The length of the portions that can be sampled, meaning the length of the data window, is in the order of 40 waves at the received signal frequency, which in this case means around 13 $\mu$s. As the number of data points in the window is equal to the product of the length of the data window and the clock frequency, in this example there are 260 points. A window function, such as a Humming window, can be applied to the data array or the data points can be converted to a number that is a power of two, for example 256 points, to adapt it to a fast-Fourier-transformation algorithm. The Fourier transformation is repeated with the data window being shifted depthwise in the specimen 16, i.e., in the depthwise direction of the data array. In this example, the pitch of the shifts is a very short distance of 1.25 mm. The time period $\Delta t_0$ required for the sonic wave to traverse this short distance and return when the sonic velocity in the specimen 16 is 1500 m/s is about 1.6 $\mu$s. For simplicity in the following explanation, the value of one-half the time period $\Delta t_0$ will be regarded as equal to the time period $\Delta t$ appearing in equation (16). With the shifting of the data window, the received signals are sampled at time period $\Delta t_0$ intervals and Fourier transformations are carried out, one after another. The results of the Fourier transformations are complex numbers, and the power spectrum $P(\omega)$ and the phase angle $\phi(\omega)$ can be calculated from the real part $R_e(\omega)$ and the imaginary part $I_m(\omega)$.

$$P(\omega) = R_e^2(\omega) + I_m^2(\omega) \qquad (33)$$

$$\phi(\omega) = \arctan\{I_m(\omega)/R_e(\omega)\} \qquad (34)$$

When pump pulse and probe pulse superposed in the phasal relationship C shown in FIG. 1 (a) or the phasal relationship D shown in FIG. 1 (b) propagate in the specimen 16, the part of the received signal obtained from scattering in the region of interest (hereinafter "ROI"), that is, the power spectrum of an array of data sampled by means of a data window located at a depth corresponding to that of the ROI, can be shown using the following type of simple propagation model.

$$P\pm(\omega) = |\{H\pm(\omega) \cdot S\pm(\omega) \cdot G(\omega) \cdot T(\omega)\} \otimes W(\omega)|^2 \quad (35)$$

Here, $S\pm(\omega)$ is the sonic scattering characteristics in the ROI; $G(\omega)$ is linear propagation attenuation along the return path; $T(\omega)$ is the frequency characteristic of the receiving system; $\otimes$ $W(\omega)$ is convolution arising from the window function; the + of the ± is sonic transmission in phasal relationship C and the − is sonic transmission in phasal relationship D.

Figure 1B:
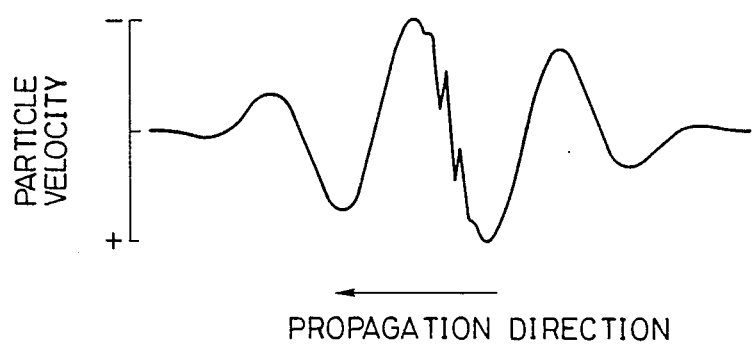

In this kind of propagation model, a sonic wave having a phasal relationship C as in FIG. 1 (a) is transmitted into the designated ROIs in specimen 16, the power spectrum $P+(\omega)$ is obtained and then, after a transmission interval $T_0$, a sonic wave having a phasal relationship D, as in FIG. 1 (b), is transmitted and the power spectrum $P-(\omega)$ obtained, and the ratio of the two power spectra is estimated logarithmically. The length of the transmission interval $T_0$ should be one that is normally used in an ultrasonic diagnostic apparatus, for example from several hundred microseconds up to 1 ms. In the following equation, if the difference between the sonic scattering characteristics $S_+(\omega)$ and $S_-(\omega)$, and the window function has little influence, the terms $S_\pm(\omega)$, $G(\omega)$, $T(\omega)$ and $W(\omega)$ are all cancelled and the left side becomes equal to the spectral ratio $R(\omega)$ shown on the left side of equation (30).

$$\ln\{P-(\omega)/P+(\omega)\} = 2\ln\{H-(\omega)/H+(\omega)\} \quad (36)$$
$$= 2R(\omega)$$

The relationship between the spectral ratio $R(\omega)$ and the various acoustic characteristics is as already shown by equations (29) to (32). In the signal processor 9, the acoustic characteristics are computed on the basis of these relationship equations.

Figure 4:
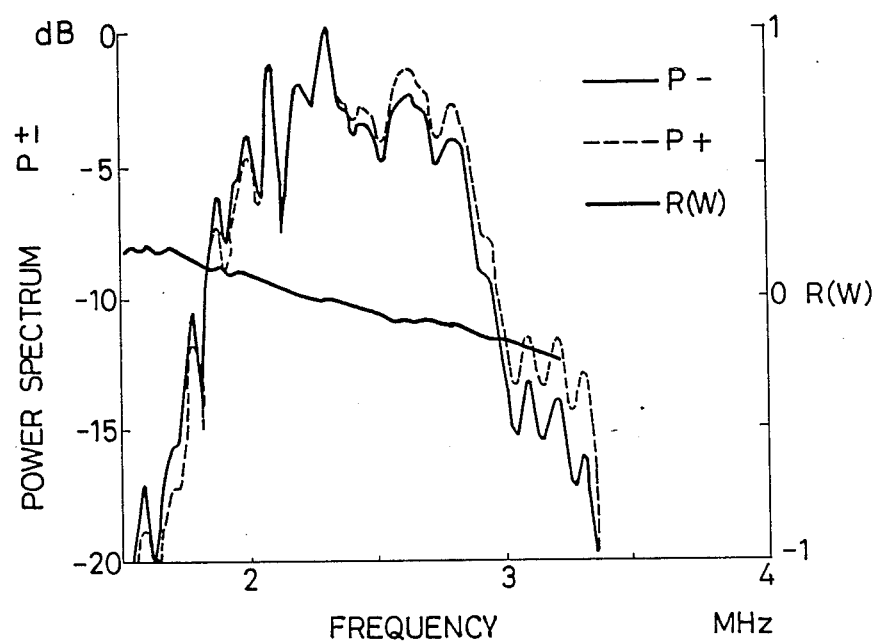
FIG. 4 shows the spectral ratio of the received signals obtained in an embodiment of the invention.

FIG. 4 shows an example of actual measured values for the power spectrum $P\pm(\omega)$ and the spectral ratio $R(\omega)$, using as the specimen 16 an ultrasonic test phantom made up to resemble the liver. The spectral ratio $R(\omega)$ has quite a ripple component that is included as noise and which has an adverse effect on the determination of the crossover frequency $\omega_x$. To reduce this, a spectral ratio $R(\omega)$ obtained in the vicinity of the crossover frequency $\omega_x$, in a 2 to 3 MHz range in this example, is approximated using an approximation function $f(\omega)$ constituted of 1st or 2nd order functions, and the crossover frequency $\omega_x$ is determined from the frequency at which the approximation function $f(\omega)$ becomes zero. The method of least squares or the like can be used to select the approximation function $f(\omega)$. Next, the frequency differential of the spectral ratio $R(\omega)$, that is, the degree of spectral separation DSS, is obtained. In practice, the degree of spectral separation DSS is also obtained from the differential of the approximation function $f(\omega)$. In equation (32), the DSS and $\omega_x$ are measurable quantities, and as the pump wave angular frequency $\Omega$, probe pulse center angular frequency $\omega_c$ and the spectral dispersion $\sigma_0^2$ are known quantities, if the quantity n that stands for the frequency dependence of the attenuation, shown in equation (16), can be designated, the propagation delay time difference $\pi_i$ can be found. There are known n values for each internal organ, for example, 1 or 2 in the case of the liver and 1 or 3 in the case of spleen, so for each ROI or data window, a corresponding n value can be designated. When the abdominal region is to be measured, even designating a value for n of n=1.2 for all ROIs will not give rise to a large error.

Propagation delay time difference $\tau_i$ can be measured by conventional techniques, so the value of n can also be obtained from equation (32). For example, when a pulse having a phasal relationship A (FIG. 9 (a)) is transmitted, the propagation velocity of the pump wave becomes higher at portions of the wave where the positive particle velocity is high, and as a result the overall propagation delay time for the probe wave is shortened. This change in propagation delay time corresponds to a phase shift in the frequency region. In an actual measurement, in the case of a phasal relationship A transmission, the received signals are sampled using a data window, and the sampled data is subjected to Fourier transformation and the phase $\phi(\omega)$ thereof obtained. Next, after a transmission interval $T_0$ the phase $\phi(\omega)$ in respect of a phasal relationship B is obtained and the difference in the phase $\phi(\omega)$ thus obtained in the case of a phasal relationship A compared to that obtained in the case of a phasal relationship B, that is, the phase shift, is obtained, and the functional differential of this phase shift, and propagation delay time difference $\tau_i$, as a group delay time, can be obtained. Because there is a large error with this method, preferably the measurements are repeated a large number of times and the obtained propagation delay time differences $\tau_i$ are averaged. Using the $\tau_i$ thus-obtained, the degree of spectral separation DSS and the crossover frequency $\omega_x$ obtained through measurements according to the present invention, and the known quantities $\Omega$, $\omega_c$ and $\sigma_0^2$, the value of n can be found from equation (32).

Thus, by using either an assumed value for the frequency dependency characteristic of attenuation n or a pre-measured n value, the propagation delay time difference value $\tau_j$ ($1 \leq j \leq i$) can be obtained. When the water submersion method is used, values for propagation delay time difference $\tau_j$ for each propagation depth in the water can be kept as prior data, and from the information on depths from the surface of the specimen 16, the value of the surface propagation delay time difference $\tau_j$ may be determined.

Next, the method of obtaining the attenuation coefficient $a_j$ shown in equation (16) from the crossover frequency $\omega_{xj}$ and the distribution of the propagation delay time difference $\tau_j$, and the method of obtaining the distribution of the associated coefficient of non-linearity $\beta_j'$ shown in equations (20) to (22) will be described. First, by substituting the values of $\omega_{xj}$ and $\tau_i$ in equation (31), the quantity $(a_- - a_+)_i$ relating to attenuation can be obtained. Using equation (29), this quantity can be shown as in the following equation.

$$(a_- - a_+)_i = (1 + \Omega\tau_i)^n \sum_{j=1}^{i} \frac{a_j}{1 + \Omega\tau_{j-1}} - \quad (37)$$

$$(1 - \Omega\tau_i)^n \sum_{j=1}^{i} \frac{a_j}{1 - \Omega\tau_{j-1}}$$

In equation (37), as $(a_- - a_+)_i$ and $\tau_j$ are measurable quantities and $\Omega$ is a known quantity, by designating a value for n, a simultaneous equation relating to $\tau_j$ ($1 \leq j \leq i$) can be obtained. In this simultaneous equation, when i=1 the only unknown is $a_1$, which can be obtained immediately, and when i=2, as $a_1$ has already been found, only $a_2$ is unknown, and this also can be obtained immediately. Thus, $a_1$ can be obtained by consecutively increasing by i, from i=1.

Using any of equations (20) to (22), the distribution of associated coefficient of non-linearity $\beta_j'$ can be obtained from the propagation delay time difference $\tau_j$. If equation (21) is used, it is necessary to obtain the distribution $U_{oj}$ of the pump pulse velocity amplitude in the direction of propagation, but this cannot be measured directly in vivo. However, if a typical in vivo sonic attenuation characteristic of 0.7 dB/MHz·cm is assumed, by correcting measured values for particle velocity distribution obtained in water, the particle velocity amplitude $U_{oj}$ of the pump pulse in the body can be estimated quite precisely. The particle velocity amplitude $U_{oj}$ values obtained thus beforehand can be kept as data and the associated coefficient of non-linearity $\beta_j'$ distribution can be found. It is also possible to use a method whereby particle velocity amplitude $U_{oj}$ values in water, including when the immersion method is used, can be kept as data and the particle velocity amplitude $U_{oj}$ values corrected in accordance with the type of the specimen 16.

Figure 5:
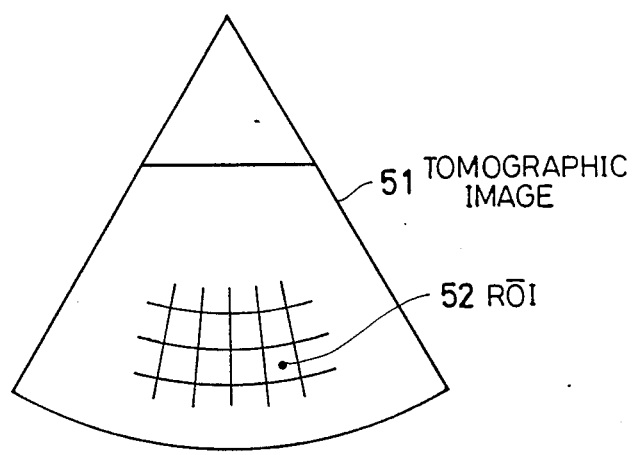
FIG. 5 shows an example of the boundary line of a region of interest.

Thus, the attenuation characteristic $a_j$ along the propagation path of the probe pulse and the distribution of the associated coefficient of non-linearity $\beta_j'$ can be obtained. In the specimen 16, these acoustic characteristic values can be regarded as average values in regions corresponding to the data window. Generally, when the problem is the acoustic characteristic values of a specific region on a tomographic image, a hypothetical region, the ROI, is set on the tomographic image, and average values for the acoustic characteristics are sought. FIG. 5 shows an example of the boundary lines of a multiplicity of ROIs 52 displayed on a fan-shaped scanning tomographic image 51. As will become apparent, the boundary lines form part of the fan shape. In this example, the dimensions of the ROIs 52 are around 1 cm in the depthwise direction of propagation, and around 1 cm in a direction perpendicular thereto. In fact, numerous acoustic scanning lines pass through the ROIs 52, and with respect also to the data windows on these acoustic scanning lines, many are overlap on the ROIs 52. To find average acoustic characteristic values of the ROIs 52 from the numerous acoustic characteristic values corresponding to the numerous data windows, acoustic characteristic values corresponding to acoustic scanning lines passing through the central part of the ROIs 52, or acoustic characteristic values corresponding to acoustic windows which overlap the ROIs 52 in many places can be weighted, for example, and the averages then obtained. With the signal processor 9, acoustic characteristic values can be thus obtained from the power spectra of the received signals.

Figure 6:
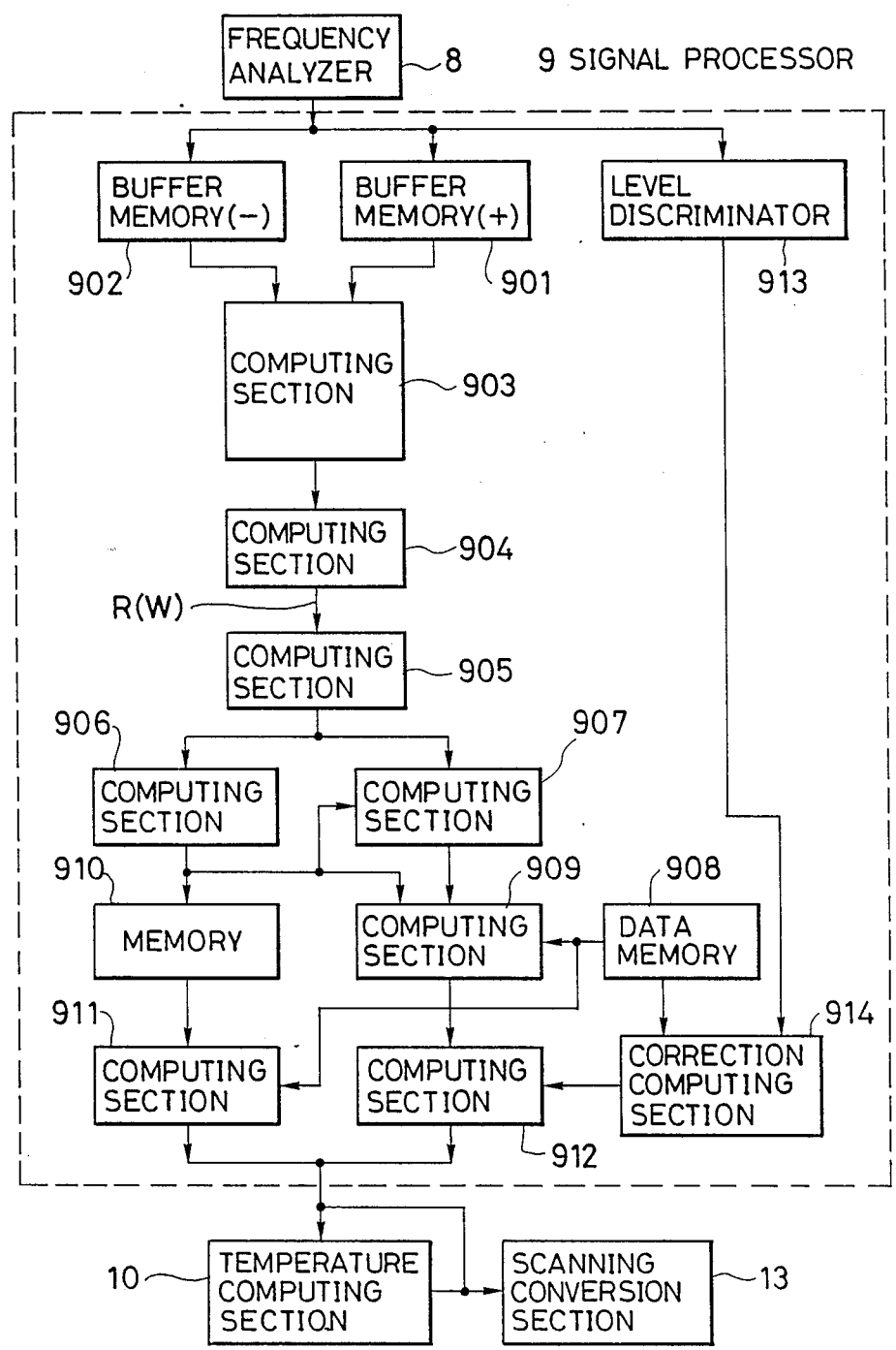
FIG. 6 is a block diagram showing details of the functional parts of an example of the signal processor used in the ultrasonic temperature measurement apparatus.

FIG. 6 is a block diagram showing details of the functional parts of an example of the signal processor 9. In FIG. 6, 901 and 902 are buffer memories for storing the power spectra of the received signals obtained by the frequency analyzer 8. The power spectrum $(P_+)_j (1 \leq j \leq i)$ obtained when the probe pulse and pump pulse are transmitted in a phasal relationship C (see FIG. 1 (a)) is stored in the buffer memory 901, and the power spectrum $(P_-)_j$ corresponding to a phasal relationship D (see FIG. 1 (b)) is stored in the buffer memory 902. (Here, j denotes the depthwise position of the data window.) The frequency range of a spectrum obtained from the fast Fourier transformation of a 256-point data array obtained at a sampling clock of 20 MHz is from −10 MHz to 10 MHz, and the spacing thereof becomes 80 KHz. In subsequent signal processing, the requisite frequency range is around 1.5 MHz to 4 MHz, so there is no objection to limiting the number of usable power spectrum points on the frequency axis to around 30. Numeral 903 denotes a computing section for performing divisions on the frequency components corresponding to each of the power spectra $(P_+)_j$ and $(P_-)_j$ in which the value of j is the same; 904 is a computing section for computing the logarithms of the output of the computing section 903. The output of the computing section 904 is equal to the spectral ratio $R(\omega)$ of equation (36). Numeral 905 denotes a computing section that generates a coefficient of polynomial approximation expression $f(\omega)$ for the spectral ratio $R(\omega)$. As is apparent from equation (30), spectral ratio $R(\omega)$ can be closely approximated with a second-order function of $\omega$ that passes through the origin, and the polynomial approximation expression $f(\omega)$ can be shown by the following equation, for example.

$$f(\omega) = a \cdot \omega_2 + b \cdot \omega \qquad (38)$$

By using spectral ratio $R(\omega)$, the undetermined coefficients a and b can be determined by the method of least squares or the like. Numeral 906 denotes a computing section that computes the crossover frequency $\omega_x$ on the basis of the coefficients "a" and "b" of the output of the computing section 905. In this case, from equation (38) crossover frequency $\omega_x$ becomes $-b/a$. Numeral 907 is a computing section for obtaining the slope of the spectral ratio $R(\omega)$ at the crossover frequency $\omega_x$ shown in equation (32), that is, the degree of spectral separation DSS; the degree of spectral separation DSS can be obtained from the crossover frequency $\omega_x$ already obtained and coefficients "a" and "b" by differentiating equation (38). Numeral 908 denotes a data memory for storing data required for subsequent computations. For example, n representing the frequency dependency of the attenuation, the angular frequency $\Omega$ of the pump wave, the center angular frequency $\omega_c$ of the probe pulse, spectral dispersion $\sigma_0^2$ and the distribution of the pump wave particle velocity amplitude $U_{oj}$ are stored in the memory 908.

A computing section 909 is for obtaining propagation delay time difference $\tau_j$ in accordance with equation (32) on the basis of the outputs of computing sections 906 and 907 and data memory 908. Numeral 910 denotes a memory for storing crossover frequency $\omega_{xj}$ output from the computing section 906 and the propagation delay time difference $\tau_j$ from the computing section 909. Numeral 911 is a computing section for obtaining the attenuation coefficient $a_j$ in accordance with equations (31) and (37) on the basis of the $\omega_{xj}$ and $\tau_j$ stored in memory 910. The computing section 911 obtains the attenuation coefficient $a_j$ starting from a low-order j, and the attenuation coefficients $a_j$ already obtained are stored in memory 910 in order to obtain the next attenuation coefficient $a_{j+1}$. Numeral 912 denotes a computing section that obtains the variations in $\Delta T_j$ in propagation delay time difference $\tau_j$ on the basis of equation (18) and then the associated coefficient of non-linearity $\beta_j'$ on the basis of equations (21) and (22). When for example equation (21) is used, the distribution of the particle velocity amplitude $U_{oj}$ of the pump pulse stored in the data memory 908 is utilized. In cases where the attenuation of the pump wave amplitude is not uniform, such as when the water immersion method is used, the particle velocity amplitude $U_{oj}$ values in the data memory 908 may be changed. Numeral 913 denotes a level discriminator that detects the position of the surface of the specimen 16 when the water immersion method is employed. After the probe pulse has been transmitted, with respect to the time at which the power spectrum output of the frequency analyzer 8 exceeds a certain level, if prior to that time the pump pulse is regarded as propagating in water and after that time the pump pulse is regarded as propagating in the specimen 16, the level 913 outputs data window position information k corresponding to the said time. Numeral 914 denotes a correction computing section which, on the basis of the position information output by the level discriminator 913, corrects the particle velocity amplitude $U_{oj}$ values stored in the data memory 908 with respect to $j>k$ portions, taking into account the sonic attenuation characteristic of the pump wave frequency, without changing the $U_{oj}$ values of $1 \leq j \leq k$ portions. Computing section 912 may also be used to obtain the associated coefficient of non-linearity $\beta_j'$, using the thus-corrected particle velocity amplitude $U_{oj}$.

Figure 7A:
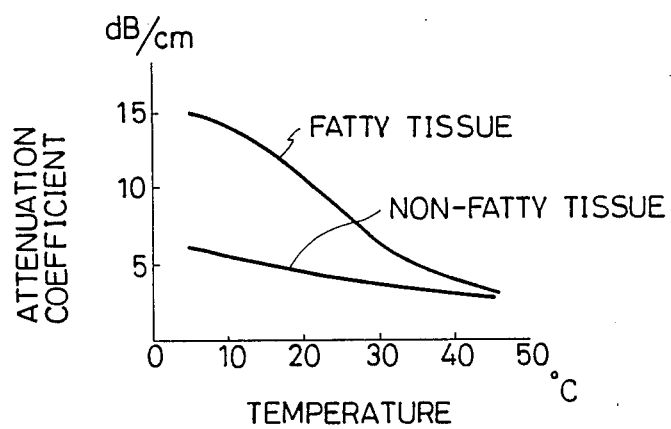
FIGS. 7 (a) and (b) show the attenuation coefficient and the temperature dependency of the sonic velocity in living tissue.
Figure 7B:
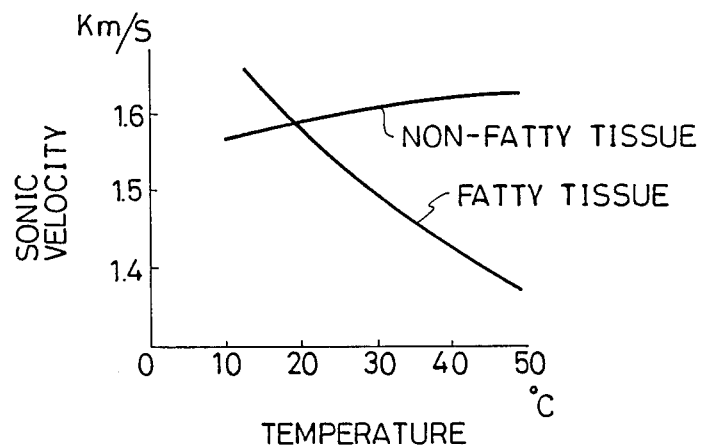

The attenuation coefficient $a_j$ or associated coefficient of non-linearity $\beta_j'$ thus obtained are sent to the temperature computing section 10 and the scanning conversion section 13. Or, the attenuation coefficient $a_j$ and associated coefficient of non-linearity $\beta_j'$ may be obtained with respect to a multiplicity of acoustic scan lines and the average values of the attenuation coefficients $a_j$ and of the associated coefficients of non-linearity $\beta_j'$ in the ROIs obtained and sent to the scanning conversion section 13. The temperature computing section 10 computes temperature changes in each ROI based on the temperature dependency characteristic of the attenuation coefficient or associated coefficient of non-linearity. FIG. 7 shows a representative example of the temperature dependency of the attenuation coefficient and sonic velocity in soft tissues. As is apparent from FIG. 7, the temperature dependency of the attenuation coefficient is relatively high, and that of the sonic velocity is low. Furthermore, there is quite a difference between the temperature dependency characteristics of fatty tissue and non-fatty tissue. These temperature dependencies are not expressed when a simple 1st-order function of temperature T is used, from which it can be seen that an approximation based on a high-order polynomial expression is all the more preferable. With respect to the non-linearity parameter B/A, it is considered that the temperature dependency thereof is quite small, therefore the temperature dependency of the associated coefficient of non-linearity $\beta_j$ can be considered as being controlled by the temperature dependency of the sonic velocity in the denominator.

FIG. 8 is a block diagram of the functional parts of one example of the temperature computing section 10. In the drawing, 1001 is a memory prepared for each ROI in which the initial-state acoustic characteristic values are stored. Here, initial state refers to a state of normal body temperature prior to heating the body, such as in the application of hypothermia. Next, attenuation coefficient and associated coefficient of non-linearity values stored in the memory 1001 are compared in the data reference section 11. The attenuation coefficient and associated coefficient of non-linearity are useful diagnostic parameters. For example, there is a large difference between values obtained in the case of fatty tissue and non-fatty tissue. Therefore, by referencing the attenuation coefficient and associated coefficient of non-linearity in the data reference section 11, the nature of the tissue can be judged. Thus, from reference to the memory 1001, the temperature dependency characteristics of the acoustic characteristics in the tissues in each ROI can be designated. If $\tau(T)$ is the temperature characteristic, $\tau(T)$ is a 1st or high-order polynomial expression that satisfies the following equation.

$$a(T) = a_0 - \tau(T) \tag{39}$$

Here, $a_0$ is the initial-state acoustic characteristics and $a(T)$ is the acoustic characteristics after a change from the initial state of T degrees centigrade.

The coefficient values of each order of the polynomial expression are sufficient for the designation of $\tau(T)$, and are stored in the data reference section 11 in the form of coefficients. The coefficient values of the temperature dependency $\tau(T)$ referred to for each ROI are stored in the memory 1002. In this case, temperature dependency $\tau(T)$ designates only the attenuation coefficient. In the computing section 1003 the attenuation coefficient of each ROI at each temperature is computed at an appropriate temperature pitch, for example 1 degree centigrade, over an appropriate temperature range, for example 35° C. to 50° C., based on coefficient values stored in the memory 1002 and initial-state attenuation coefficients stored in the memory 1001, and the computed attenuation coefficients are stored in memory 1004. Next, the attenuation coefficient following heating is stored in memory 1005. The computing section 1006 compares the data stored in memory 1005 to ascertain if it corresponds to any of the data stored in memory 1004, that is, to see how many changes it corresponds to. The computing section 1006 performs this comparison for each ROI, and temperature change values are stored in memory 1007. The values of the temperature changes T thus obtained are sent to the scanning conversion section 13, enabling a two-dimensional image of the temperature distribution to be obtained.

In the above description, temperature changes are computed with respect to all ROIs and are displayed as images. However, it is to be understood that temperature changes could just as well be computed with respect to designated ROIs alone, and the results of the computation could be displayed numerically. Furthermore, even displaying in image form acoustic characteristics such as the distribution of the attenuation coefficient and the distribution of the associated coefficient of non-linearity, obtained partway through the signal processing, has a high diagnostic significance. The obtained acoustic characteristic values, including the value of the frequency dependency characteristic n of the ultrasonic wave attenuation, could also be displayed. Also, the crossover frequency and the dependency in the depth direction of propagation of the degree of spectral separation could be displayed, for these also show the acoustic characteristic values of the propagation medium. In the case of a specimen which is homogeneous and the temperature dependency characteristics of which are known, with respect to the temperature computation, even if the known temperature dependency characteristics are prepared beforehand and applied to all ROIs, highly accurate measurement can still be realized.

As described in the foregoing, in the present invention, by superposing the probe pulse centroid on the pump pulse wave particle acceleration peak portions, a peak particle velocity on a par with the particle velocity of the pump pulse itself can be generated by compounding the two pulses, with no fear of the probe pulse being abnormally distorted and with a high level of safety with respect to the living body. Also, the ultrasonic attenuation characteristic can be obtained at the same time as the associated coefficient of non-linearity, and use of the these two acoustic characteristic values enables a high level of diagnostic and measurement accuracy to be achieved.

What is claimed is:

1. An acoustic characteristic measurement method comprising the steps of:
    transmitting from the same side of a specimen into the specimen an ultrasonic probe pulse signal and a pump pulse signal of lower frequency than that of said probe pulse signal, with the centroid of said probe pulse signal superposed on a portion of said pump pulse signal where the particle acceleration of said pump pulse signal is at a peak;
    receiving reflections of the transmitted signal from at least two reflecting points that are at different depths in the specimen;
    frequency-analyzing the received signals to obtain a spectral ratio; and
    calculating from said spectral ratio a distribution in specimen of a crossover frequency and a degree of spectral separation which are acoustic characteristics.

2. The acoustic characteristic measurement method according to claim 1 wherein amount of spectral shift in the received signals is obtained, and an amount of phase shift and the degree of spectral separation are used to measure a frequency dependency characteristic of a sonic attenuation characteristics in a specimen.

3. The acoustic characteristic measurement method according to claim 2 wherein an associated non-linearity coefficient is obtained from the degree of spectral separation.

4. The acoustic characteristic measurement method according to claim 2 wherein a sonic attenuation coefficient is obtained from the crossover frequency and the degree of spectral separation.

5. The acoustic characteristic measurement method according to claim 2 wherein an associated non-linearity coefficient is obtained from the degree of spectral separation and a coefficient of sonic attenuation is measured from the crossover frequency.

6. The acoustic characteristic measurement method according to claim 1 wherein an associated non-linearity coefficient is obtained from the degree of spectral separation.

7. The acoustic characteristic measurement method according to claim 1 wherein a sonic attenuation coefficient is obtained from the crossover frequency and the degree of spectral separation.

8. The acoustic characteristic measurement method according to claim 1 wherein an associated non-linearity coefficient is obtained from the degree of spectral separation and a coefficient of sonic attenuation is measured from the crossover frequency.

9. A temperature measurement method comprising the steps of:
    transmitting from the same side of a specimen into the specimen an ultrasonic probe pulse signal and a pump pulse signal of a lower frequency than that of said probe pulse signal, with the centroid of said probe pulse signal superposed on a portion of said pump pulse signal where the particle acceleration of said pump pulse signal is at a peak;
    receiving reflections of the transmitted signal from at least two reflecting points that are at different depths in the specimen;
    frequency-analyzing the received signals to obtain a spectral ratio;
    calculating a distribution in the specimen of a crossover frequency and a degree of spectral separation from said spectral ratio;
    calculating a sonic attenuation coefficient and an associated coefficient of non-linearity from the distribution of the crossover frequency and the degree of spectral separation obtained; and
    comparing the sonic attenuation coefficient and associated coefficient of non-linearity obtained with a reference sonic attenuation coefficient and a reference coefficient of non-linearity stored in advance to calculate a temperature distribution in the specimen.

10. The temperature measurement method according to claim 9 wherein a change in temperature in the specimen before and after the heating thereof is measured on the basis of a temperature dependency characteristic of an attenuation coefficient referenced using a value of an associated coefficient of non-linearity in the region of interest.

11. An acoustic characteristic measurement apparatus comprising:
    an ultrasonic wave transducer for transmitting from the same side of a specimen into the specimen an ultrasonic probe pulse signal and a pump pulse signal of a lower frequency than that of said probe pulse signal with the centroid of said probe pulse signal superimposed on a portion of said pump pulse signal where the particle acceleration of said pump pulse signal is at a peak, said ultrasonic wave transducer having means for receiving reflections of the transmitted signal from at least two reflecting points that are at different depths in the specimen;
    means for frequency-analyzing the received signals; and
    signal processing means for calculating a spectral ratio from the analyzed frequency and calculating from the calculated spectral ratio a distribution in a specimen of a crossover frequency and a degree of spectral separation which are acoustic characteristics.

12. The acoustic characteristic measurement apparatus according to claim 11 wherein the signal processing means also computes at least one of the associated non-linearity coefficient and sonic attenuation coefficient from the crossover frequency and the degree of spectral separation.

13. A temperature measurement apparatus comprising:
    an ultrasonic wave transducer for transmitting from the same side of a specimen into the specimen an ultrasonic probe pulse signal and a pump pulse signal of a lower frequency than that of said probe pulse signal, with the centroid of said probe pulse signal superimposed on a portion of said pump pulse signal where the particle acceleration of said pump pulse signal is at a peak, said ultrasonic wave transducer having means for receiving reflections of the transmitted signal from at least two reflecting points that are at different depths in the specimen;
    means for frequency-analyzing the received signals;

signal processing means for calculating a spectral ratio from the analyzed frequency and calculating from the calculated spectral ratio a distribution in a specimen of a crossover frequency and a degree of spectral separation which are acoustic characteristics;

calculating means for calculating a sonic attenuation coefficient and an associated coefficient of non-linearity from the distribution of the crossover frequency and the degree of spectral separation obtained; and a calculator for comparing the sonic attenuation coefficient and associated coefficient of non-linearity obtained with a reference sonic attenuation coefficient and a reference coefficient of non-linearity stored in advance to calculate the temperature distribution in the specimen.

14. The temperature measurement apparatus according to claim 13, wherein the temperature computing section is provided with a data reference section having stored temperature dependency characteristic of acoutic characteristics and a temperature of the specimen is measured from an output of the signal processing means on the basis of the temperature dependency characteristic.

* * * * *